(12) United States Patent
Wasielewski

(10) Patent No.: US 10,080,663 B2
(45) Date of Patent: *Sep. 25, 2018

(54) KNEE PROSTHESIS INCLUDING ROTATABLE SPINE

(71) Applicant: Ray C. Wasielewski, New Albany, OH (US)

(72) Inventor: Ray C. Wasielewski, New Albany, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/585,781

(22) Filed: May 3, 2017

(65) Prior Publication Data

US 2017/0333195 A1    Nov. 23, 2017

Related U.S. Application Data

(63) Continuation of application No. 14/933,210, filed on Nov. 5, 2015, now Pat. No. 9,668,870, which is a continuation of application No. 14/189,205, filed on Feb. 25, 2014, now Pat. No. 9,216,088.

(60) Provisional application No. 61/783,279, filed on Mar. 14, 2013.

(51) Int. Cl.
*A61F 2/38* (2006.01)
*A61F 2/30* (2006.01)

(52) U.S. Cl.
CPC .............. *A61F 2/385* (2013.01); *A61F 2/389* (2013.01); *A61F 2/3836* (2013.01);
(Continued)

(58) Field of Classification Search
CPC ...... A61F 2/38; A61F 2/34; A61F 2/32; A61F 2/389; A61F 2/3868
See application file for complete search history.

(56) References Cited

U.S. PATENT DOCUMENTS 6,719,800 B2    4/2004  Meyers et al.
6,986,791 B1    1/2006  Metzger
(Continued)

FOREIGN PATENT DOCUMENTS

EP    0913132 A1    5/1999
EP    0970667 A1    1/2000
(Continued)

OTHER PUBLICATIONS

"U.S. Appl. No. 14/189,205, Final Office Action dated Jul. 7, 2015", 7 pgs.
(Continued)

*Primary Examiner* — Jason-Dennis Stewart
(74) *Attorney, Agent, or Firm* — Schwegman Lundberg & Woessner, P.A.

(57) ABSTRACT

A knee joint prosthesis is disclosed. The knee joint prosthesis can include a tibial baseplate, a tibial insert, and a spine. The tibial baseplate can include a tibial plateau, having a proximal surface and an opposing distal surface, and a tibial stem extending from the distal surface of the tibial plateau. The tibial insert can be located on the proximal surface of the tibial plateau and can include an aperture. The spine can extend through the aperture of the tibial insert and into a cavity of the tibial stem, from the proximal surface of the tibial plateau. The spine can be rotatable with respect to the tibial baseplate and the tibial insert. The knee joint prosthesis can further include a femoral component including a posteriorly-located femoral cam. The posteriorly-located femoral cam can engage the spine during movement of the knee joint prosthesis.

19 Claims, 4 Drawing Sheets

(52) U.S. Cl.
CPC .......... *A61F 2/3886* (2013.01); *A61F 2/3859* (2013.01); *A61F 2/3868* (2013.01); *A61F 2002/30332* (2013.01); *A61F 2002/30364* (2013.01); *A61F 2002/30474* (2013.01); *A61F 2002/30604* (2013.01); *A61F 2210/0076* (2013.01)

(56) References Cited

U.S. PATENT DOCUMENTS

| | | |
|---|---|---|
| 9,216,088 B2 | 12/2015 | Wasielewski |
| 9,668,870 B2 | 6/2017 | Wasielewski |
| 2011/0178606 A1 | 7/2011 | Deffenbaugh et al. |
| 2014/0277534 A1 | 9/2014 | Wasielewski |
| 2016/0051366 A1 | 2/2016 | Wasielewski |

FOREIGN PATENT DOCUMENTS

| | | |
|---|---|---|
| EP | 1086667 A1 | 3/2001 |
| WO | WO-2012062856 A1 | 5/2012 |
| WO | WO-2014143538 A1 | 9/2014 |

OTHER PUBLICATIONS

"U.S. Appl. No. 14/189,205, Non Final Office Action dated Feb. 20, 2015", 7 pgs.

"U.S. Appl. No. 14/189,205, Notice of Allowance dated Aug. 14, 2015", 8 pgs.

"U.S. Appl. No. 14/189,205, Response filed Jun. 16, 2015 to Non-Final Office Action dated Feb. 20, 2015", 14 pgs.

"U.S. Appl. No. 14/189,205, Response filed Aug. 5, 2015 to Final Office Action dated Jul. 7, 2015", 13 pgs.

"U.S. Appl. No. 14/933,210, Non Final Office Action dated Oct. 18, 2016", 5 pgs.

"U.S. Appl. No. 14/933,210, Notice of Allowance dated Feb. 3, 2017", 8 pgs.

"U.S. Appl. No. 14/933,210, Preliminary Amendment filed Nov. 6, 2015", 6 pgs.

"U.S. Appl. No. 14/933,210, Response filed Dec. 1, 2016 to Non Final Office Action dated Oct. 18, 2016", 8 pgs.

"International Application Serial No. PCT/US2014/018228, International Preliminary Report on Patentability dated Sep. 24, 2015", 8 pgs.

"International Application Serial No. PCT/US2014/018228, International Search Report dated Apr. 30, 2014", 4 pgs.

"International Application Serial No. PCT/US2014/018228, Written Opinion dated Apr. 30, 2014", 6 pgs.

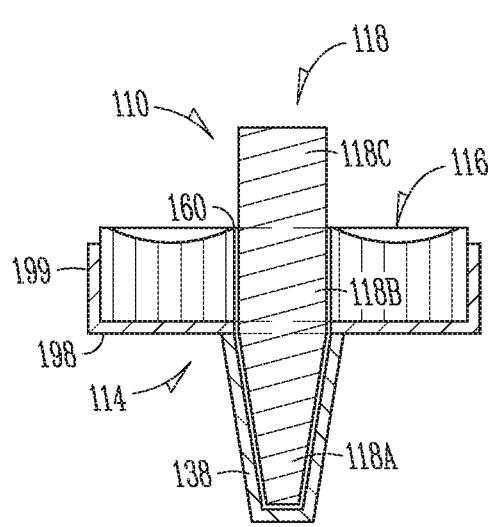
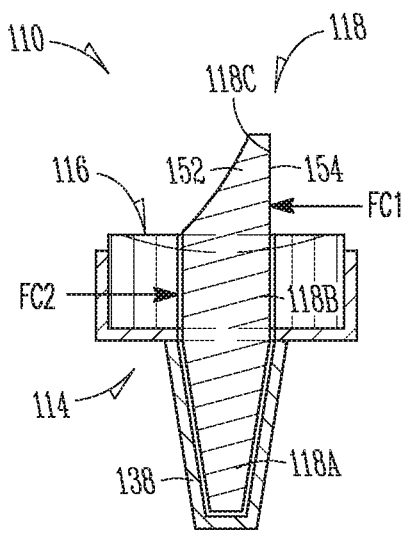
*FIG. 2A*  *FIG. 2B*
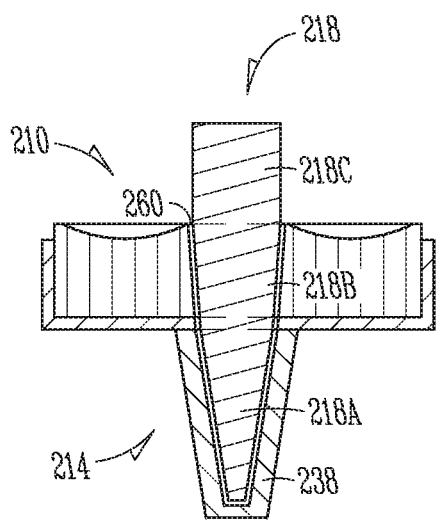
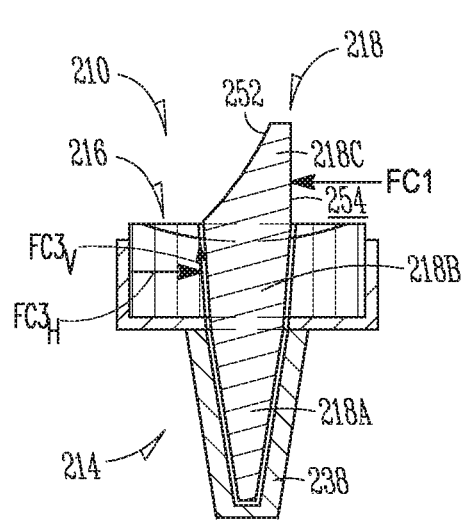
*FIG. 3A*  *FIG. 3B*

KNEE PROSTHESIS INCLUDING ROTATABLE SPINE

CLAIM OF PRIORITY

This application is a continuation of U.S. patent application Ser. No. 14/933,210, filed on Nov. 5, 2015, now issued as U.S. Pat. No. 9,668,870, which is a continuation of U.S. patent application Ser. No. 14/189,205, filed on Feb. 25, 2014, now issued as U.S. Pat. No. 9,216,088, which claims the benefit of U.S. Provisional Patent Application Ser. No. 61/783,279, filed on Mar. 14, 2013, the benefit of priority of each of which is claimed hereby, and each of which are incorporated by reference herein in its entirety

TECHNICAL FIELD

The present disclosure relates to orthopedic prostheses and, specifically, to knee prostheses.

BACKGROUND

Orthopedic prostheses are commonly utilized to repair or replace damaged bone and tissue in a human body. A knee prosthesis, for example, can include a tibial component or a femoral component to replace damaged or destroyed bone in the tibia or femur, respectively. Knee prostheses can seek to provide articulation similar to an anatomical articulation of a natural knee joint.

Total knee replacement (TKR) surgery can involve the implantation of several components meant to restore the functionality provided by a natural knee. Typical TKR components include a tibial component, a femoral component, and/or an insert or bearing component disposed between the tibial and femoral components.

In certain TKR prostheses, which are oftentimes referred to as "posterior stabilized" prostheses, a cam positioned in an intercondylar fossa of a femoral component cooperates with a spine formed in a tibial component to guide or constrain motion within predefined boundaries. Posterior stabilized prostheses can include a spine integrally formed with a tibial bearing insert (sometimes referred to as a meniscal component), which interacts with a cam formed in a femoral component to promote femoral roll back during flexion of the TKR prosthesis. Posterior stabilized prostheses can be appropriate where a posterior cruciate ligament (PCL) is torn or otherwise damaged, or where the PCL is resected during surgery.

In addition, some knee prostheses feature a hyperextension stop, which can be a posterior-facing structure formed in a femoral component configured to engage an anterior-facing surface of the tibial spine when the knee prosthesis is in a "full extension" or "hyperextension" orientation. Such a hyperextension stop can also be referred to as an anterior cam. In these knee prostheses, interaction between the femoral component and spine operates as a physical stop against extension of the knee prosthesis past a predetermined level of extension.

A natural knee experiences internal and external rotation, i.e., rotation about a generally proximal-distal axis, during flexion. Internal/external rotation can be significant in deep flexion where an asymmetric anteroposterior rollback can occur, i.e., the lateral femoral condyle rolls back faster and/or further than the medial condyle. Internal/external rotation is also significant as the natural knee approaches extension (i.e., 0-20 degrees), a phenomenon sometimes referred to as the "screw-home" mechanism. Knee prosthesis designs can seek to accommodate, promote or drive internal/external rotation mimicking the natural knee.

OVERVIEW

The present disclosure provides a knee joint prosthesis including a spine, which rotates when contacted by a posterior femoral cam. The spine can accommodate internal/external rotation of prosthesis components, while maintaining a large cam/spine surface area contact. The knee joint prosthesis can include a tibial baseplate component and a tibial insert, with the spine seated in a cavity of a stem of the tibial baseplate and extending proximally through an aperture formed in the tibial insert.

A distal portion of the spine, i.e., the portion of the spine extending through the tibial bearing and baseplate and into the cavity of the stem, can each feature a taper angle. This taper angle can be controlled to balance competing interests of free rotation and vertical stability. Free rotation, or the ability of the spine to rotate in response to a relatively small force exerted by the posterior femoral cam, can be promoted by a large taper angle (i.e., a more conical spine). Vertical stability, or the resistance of the spine to lifting out of its seat in response to a relatively large force exerted by the posterior femoral cam, can be promoted by a smaller taper angle.

To further illustrate the knee prosthesis systems disclosed herein, a non-limiting list of examples is provided here:

In Example 1, a knee joint prosthesis can comprise a tibial baseplate, a tibial insert, and a spine. The tibial baseplate can include a tibial plateau, having a proximal surface and an opposing distal surface, and a tibial stem extending from the distal surface of the tibial plateau. The tibial insert can be located on the proximal surface of the tibial plateau and can include an aperture. The spine can extend through the aperture of the tibial insert and into a cavity of the tibial stem, from the proximal surface of the tibial plateau. The spine can be rotatable with respect to the tibial baseplate and the tibial insert.

In Example 2, the knee joint prosthesis of Example 1 can optionally be configured such that the spine includes a proximal spine portion, projecting proximally from a proximal articular surface of the tibial insert, having at least one cam surface configured to articulate with a posterior femoral cam.

In Example 3, the knee joint prosthesis of any one or any combination of Examples 1 or 2 can optionally be configured such that the spine includes an intermediate spine portion, disposed within the aperture of the tibial insert, configured to rotatably articulate with a wall of the aperture.

In Example 4, the knee joint prosthesis of Example 3 can optionally be configured such that the intermediate spine portion has a shape comprising one of cylindrical, slightly tapered, or fully tapered.

In Example 5, the knee joint prosthesis of any one or any combination of Examples 1-4 can optionally be configured such that the spine includes a distal spine portion, disposed within the cavity of the tibial stem, having a tapered, substantially conical shape.

In Example 6, the knee joint prosthesis of any one or any combination of Examples 3-5 can optionally be configured such that at least one of the intermediate spine portion and the distal spine portion includes a sleeve coupled about an outer spine surface.

In Example 7, the knee joint prosthesis of any one or any combination of Examples 1-6 can optionally be configured such that the tibial insert includes a sleeve coupled to a surface of the aperture.

In Example 8, the knee joint prosthesis of any one or any combination of Examples 1-7 can optionally be configured such that the tibial stem includes a sleeve coupled to a surface of the cavity.

In Example 9, the knee joint prosthesis of any one or any combination of Examples 1-8 can optionally be configured such that the tibial insert is mobile relative to the tibial baseplate.

In Example 10, the knee joint prosthesis of any one or any combination of Examples 1-8 can optionally be configured such that the tibial insert is fixed relative to the tibial baseplate.

In Example 11, a knee joint prosthesis can comprise a femoral component including a lateral condyle, a medial condyle, and an intercondylar fossa disposed between the lateral and medial condyles. The femoral component further comprises an articular surface including respective surfaces of the lateral and medial condyles; a bone-contacting surface, opposite the articular surface, configured to affix the femoral component to a distal portion of a femur; an anterior cam, disposed anteriorly of the intercondylar fossa, extending from the bone-contacting surface; and a posterior cam disposed posteriorly of the anterior cam.

In Example 12, the knee joint prosthesis of Example 11 can optionally be configured such that the posterior cam is configured to engage a tibial spine during movement of a knee joint.

In Example 13, the knee joint prosthesis of Example 11 can optionally be configured such that the anterior cam is configured to engage a tibial spine during movement of a knee joint.

In Example 14, a knee joint prosthesis can comprise a tibial baseplate, a tibial insert, a spine, and a femoral component. The tibial baseplate can include a tibial plateau, having a proximal surface and an opposing distal surface, and a tibial stem extending from the distal surface of the tibial plateau. The tibial insert can be located on the proximal surface of the tibial plateau and can include an aperture and a proximal articular surface. The spine, rotatable with respect to the tibial baseplate and the tibial insert, can extend through the aperture of the tibial insert and into a portion of the tibial stem. The femoral component, engageable with the tibial insert, can include an articular surface, configured to abut the proximal articular surface of the tibial insert, and a posterior cam, configured to engage the spine.

In Example 15, the knee joint prosthesis of Example 14 can optionally be configured such that the spine includes a proximal spine portion, projecting proximally from the proximal articular surface of the tibial insert, having at least one cam surface configured to articulate with the posterior cam.

In Example 16, the knee joint prosthesis of any one or any combination of Examples 14 or 15 can optionally be configured such that the spine includes an intermediate spine portion, disposed within the aperture of the tibial insert, configured to rotatably articulate with a wall of the aperture.

In Example 17, the knee joint prosthesis of Example 16 can optionally be configured such that the intermediate spine portion has a shape comprising one of cylindrical, slightly tapered, or fully tapered.

In Example 18, the knee joint prosthesis of any one or any combination of Examples 14-17 can optionally be configured such that the spine includes a distal spine portion, disposed within the tibial stem, having a tapered, substantially conical shape.

In Example 19, the knee joint prosthesis of any one or any combination of Examples 16-18 can optionally be configured such that at least one of the intermediate spine portion and the distal spine portion includes a sleeve coupled about an outer spine surface.

In Example 20, the knee joint prosthesis of any one or any combination of Examples 14-19 can optionally be configured such that the tibial insert includes a sleeve coupled to a surface of the aperture.

In Example 21, the knee joint prosthesis of any one or any combination of Examples 14-20 can optionally be configured such that the tibial stem includes a sleeve coupled to a surface of the cavity.

In Example 22, the knee joint prosthesis of any one or any combination of Examples 14-21 can optionally be configured such that the tibial insert is mobile relative to the tibial baseplate.

In Example 23, the knee joint prosthesis of any one or any combination of Examples 14-21 can optionally be configured such that the tibial insert is fixed relative to the tibial baseplate. In Example 24, the knee joint prosthesis of any one or any combination of Examples 14-23 can optionally be configured such that the femoral component further includes an anterior cam disposed anteriorly of the posterior cam.

In Example 25, the knee joint prosthesis of Example 24 can optionally be configured such that the anterior cam is configured to engage the spine during movement of a knee joint.

In Example 26, the knee joint prosthesis of any one or any combination of Examples 14-25 can optionally be configured such that the posterior cam is configured to engage the spine during movement of a knee joint.

In Example 27, the knee joint prosthesis (or related methods) of any one or any combination of Examples 1-26 can optionally be configured such that all elements recited are available to use or select from.

These and other examples and features of the present knee prosthesis will be set forth in part in the following Detailed Description. This Overview is intended to provide non-limiting examples of the present subject matter—it is not intended to provide an exclusive or exhaustive explanation. The Detailed Description below is included to provide further information about the present knee prosthesis.

BRIEF DESCRIPTION OF THE DRAWINGS

FIG. 2A is a front, cross-sectional view of a fixed-bearing knee prosthesis in accordance with the present disclosure, illustrating a non-tapered intermediate spine portion.

FIG. 2B is a side, cross-sectional view of the fixed-bearing knee prosthesis of FIG. 2A.

FIG. 3A is a front, cross-sectional view of a fixed-bearing knee prosthesis in accordance with the present disclosure, illustrating a partially-tapered intermediate spine portion.

FIG. 3B is a side, elevation view of the fixed-bearing knee prosthesis of FIG. 3A.

Corresponding reference characters indicate corresponding parts throughout the several views. The exemplifications set out herein illustrate examples of the invention, and such exemplifications are not to be construed as limiting the scope of the invention in any manner.

Figures 1A, 1B:
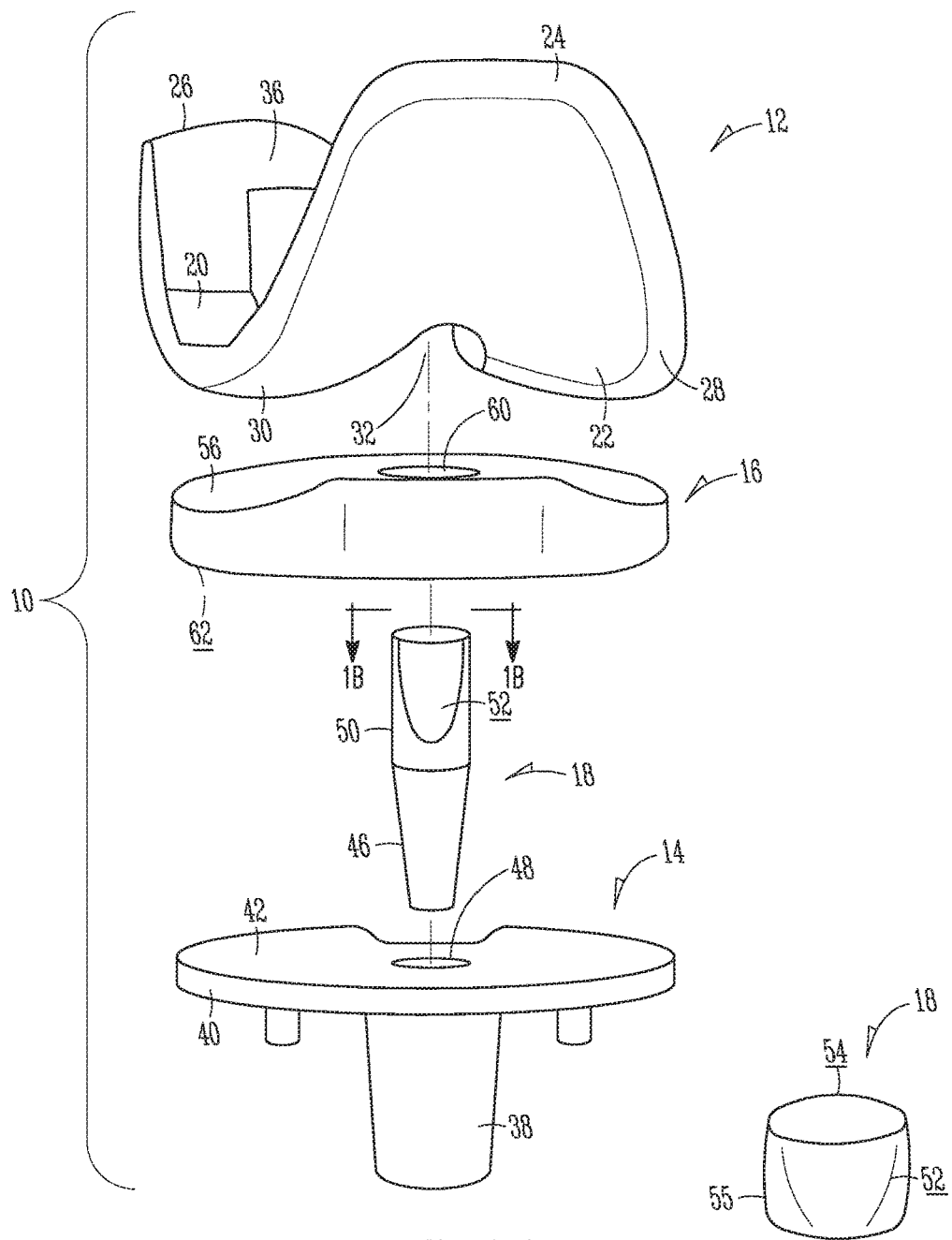
FIG. 1A is a perspective, exploded view of a knee joint prosthesis in accordance with the present disclosure.
FIG. 1B is a plan view of a tibial spine of the knee joint prosthesis shown in FIG. 1A.

In the drawings, which are not necessarily drawn to scale, like numerals can describe similar components in different views. Like numerals having different letter suffixes can represent different instances of similar components. The drawings illustrate generally, by way of example, but not by way of limitation, various examples described in the present document.

DETAILED DESCRIPTION

The present disclosure provides an orthopedic knee joint prosthesis including a spine that rotates to maintain a large-area contact with a posterior femoral cam during internal/external rotation. The rotatable spine can define a generally elongate structure extending through a tibial bearing and a tibial baseplate, and into a cavity formed in a stem extending distally from the baseplate, such that the spine rotates freely about its longitudinal axis. When the spine is contacted by the posterior femoral cam (such as in medium-to-deep flexion or in full extension), the interaction therebetween can act to automatically rotate the spine to a configuration of greatest conformity between the contacting faces. This configuration can maximize the contact area between the cam and spine, even as internal/external rotation occurs in the knee joint prosthesis.

Advantageously, the large cam/spine surface area contact minimizes wear, by maintaining low contact pressure(s) between the cam and spine. Even where substantial internal or external rotations occur, such as in deep flexion or full extension, rotation of the cam can drive concurrent rotation of the spine. These rotations can ensure a maximum area of cam/spine contact for any given level of knee flexion by ensuring the "flat" or large-radius posterior and anterior faces of the spine are presented to the corresponding surface of the posterior femoral cam or hyperextension stop (e.g., an anterior cam of a femoral component). Similarly, interaction between the posterior femoral cam and the "corners" or smaller-radius portions of the spine can be prevented.

In order to prepare a tibia and a femur for receipt of a knee joint prosthesis of the present disclosure, any suitable methods or apparatuses for preparation of the tibia and femur can be used. In the following description, "proximal" refers to a direction toward the torso of a patient, while "distal" refers to the opposite direction of proximal, i.e., away from the torso of the patient. "Anterior" refers to a direction toward the front of a patient, while "posterior" refers to the opposite direction of anterior, i.e., toward the back of the patient. While the examples described herein are described with regard to a right knee, it will be appreciated that the present disclosure is equally applicable to a left knee configuration.

FIG. 1A illustrates a knee joint prosthesis 10 including a femoral component 12, a tibial baseplate 14, a tibial insert 16, and a spine 18. The femoral component 12 and the tibial baseplate 14 can be configured to mount to a distal femur and a proximal tibia, respectively. The tibial insert 16 can rest atop a proximal surface 42 of the tibial baseplate 14 and can be disposed between the femoral component 12 and the tibial baseplate 14. The spine 18 can be coupled to the tibial baseplate 14 and can extend proximally through an aperture 60 of the tibial insert 16, such that a portion of the spine 18 extends out of the tibial insert 16 to engage with the femoral component 12, as further described below.

The spine 18, the tibial baseplate 14, and the tibial insert 16 can be manufactured from a wide range of materials including metals, plastics, polymers, polyethylene, polyurethanes, polyether ether ketone (PEEK), carbon fibers, composite materials, and combinations thereof. The spine 18 can include two or more layers of materials and can either be un-sleeved, fully sleeved, or partially sleeved. Similarly, the aperture 60 of the tibial insert 16 can either be un-sleeved, fully sleeved, or partially sleeved, and a cavity 48 in the baseplate 14 can either be un-sleeved, fully sleeved, or partially sleeved. The selection of materials and possible sleeving of one or all of the spine 18, the aperture 60, or the cavity 48 can provide greater wear resistance and minimize friction between the moving parts.

An articular surface 22 of the femoral component 12 can articulate with a proximal articular surface 56 of the tibial insert 16. In the example of FIG. 1A, a proximal surface 42 of tibial baseplate 14 can rotatably articulate with a distal surface 62 of the tibial insert 16, such that knee joint prosthesis 10 can be a mobile bearing design. As noted below, however, other examples can be a fixed-bearing design, in which the tibial insert 16 is fixed relative to the tibial baseplate 14.

The spine 18 can be a separate component that is received within a stem 38 of the tibial baseplate 14, either prior to surgical implantation of the knee prosthesis 10 or intraoperatively. The spine 18 can be rotatably coupled to the tibial baseplate 14, such that the spine 18 can be rotatable about its longitudinal axis during articulation of knee joint prosthesis 10. As described in detail below, the spine 18 can rotate during articulation of the prosthesis 10 to ensure a desired contact configuration between a posterior femoral cam 36 of the femoral component 12 and a posterior cam surface 54 (see FIG. 1B) of the spine 18.

Figure 6:
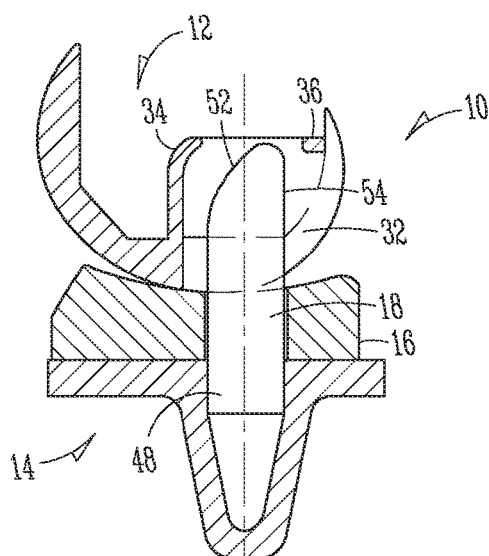
FIG. 6 is an elevation, cross-section view of a knee joint prosthesis in accordance with the present disclosure, shown in an extension orientation before a flexion motion is initiated.

As shown in FIG. 1A, the femoral component 12 can include a bone contacting surface 20 and an articular surface 22, each extending between an anterior flange 24 and a posterior side 26. The bone contacting surface 20 can be configured to affix the femoral component 12 to a distal portion of a femur, such as with bone cement and/or porous bone-ingrowth material. The femoral component 12 can include a medial condyle 28 and a lateral condyle 30, with an intercondylar fossa 32 formed between the condyles 28, 30. The articular surface 22 can be disposed generally opposite the bone contacting surface 20, and can be comprised of the exterior surfaces of the medial and lateral condyles 28, 30 as well as the exterior surface of the anterior flange 24 of the femoral component 12. The femoral component 12 can include the posterior femoral cam 36 formed at the posterior side 26. The posterior femoral cam 36 can span the medial and lateral condyles 28, 30, and can occupy the intercondylar fossa 32. FIG. 6 illustrates an example of an assembled knee joint prosthesis 10 in an elevation, cross-section view, shown in an extension orientation. The spine 18 is shown occupying the intercondylar fossa 32 of the femoral component 12. The posterior femoral cam 36 is shown in this example as not contacting the spine 18 in an extension of the knee, but, in another example, can be configured to contact the spine 18 at this point of knee articulation.

Returning to FIG. 1A, the spine 18 can include distal spine portion 46, which can be sized to be received within a correspondingly sized cavity 48 formed in tibial baseplate 14. In one example of the present disclosure, the distal spine portion 46 can have a generally conical shape. The spine 18 can further include a proximal spine portion 50 having an anterior surface 52 and a posterior cam surface 54 (see FIG. 1B). As further described below, the anterior surface 52 can be shaped and configured to provide clearance for a patella in deep flexion of the knee, and can additionally act as a hyperextension stop by cooperating with the femoral component 12 to prevent the knee prosthesis 10 from extending significantly past a full extension configuration. The posterior cam surface 54 can be shaped and configured to cooperate with the posterior femoral cam 36 to guide rollback and allow rotation of the knee joint prosthesis 10 along a specific motion profile during flexion.

As noted above, the spine 18 of the knee prosthesis 10 can be rotatable with respect to the tibial baseplate 14 and the tibial insert 16. The spine 18 can extend through the tibial plateau 40 and into the tibial stem 38. The distal portion 46 of the spine 18 can extend into a correspondingly shaped cavity 48 formed in the stem 38. In use, the proximal portion 50 of the spine 18 can be the primary point of applied forces during articulation of the prosthesis 10, as the posterior femoral cam 36 of the femoral component 12 impacts and presses against the cam surface 54 (see FIG. 1B) of the spine 18. This applied force can be counteracted by interaction between the stem 38 of the tibial baseplate 14 and the distal portion 46 of the spine 18, as further described below.

In an example, the distal portion 46 of the spine 18 can extend through substantially all of the longitudinal extent of the stem 38, while still providing a sealed distal end to prevent ingress of unwanted debris at the interface of the spine 18 and an inside wall of the cavity 48. The stem 38 can be tapered as in the illustrative example of the figures, and the distal portion 46 of the spine 18 can also be tapered to maximize the thickness of the spine 18 for a given wall thickness in the tibial stem 38.

As a result of the spine 18 extending deeply into the cavity 48, the spine 18 can advantageously provide a long moment arm and large surface area that can combine to distribute the forces exerted on the proximal portion 50 of the spine 18 (i.e., by the posterior femoral cam 36 during knee articulation) over a large surface area of the inside wall of the cavity 48. This wide distribution of forces acts to minimize pressure and friction between the distal portion 46 of the spine 18 and the inside wall of the cavity 48. This minimized friction, in turn, promotes low wear and long service life for the spine 18. Fluid can also enter the space between the cavity 48 and the spine 18 and this can also further improve tribiologics (e.g. reduced friction and wear).

Referring now to FIGS. 2A and 2B, a fixed-bearing knee prosthesis 110 can include a tibial baseplate 114, a tibial insert 116, and a spine 118. The knee prosthesis 110 can be similar to the prosthesis 10 described above, with reference numerals of prosthesis 110 having the same numerals used as the prosthesis 10 except with 100 added thereto. Structures of the prosthesis 110 correspond to similar structures denoted by corresponding reference numerals of the prosthesis 10, except as otherwise noted.

Unlike the prosthesis 10 described above, the prosthesis 110 is a fixed-bearing design, which is to say the tibial insert 116 is fixed with respect to the tibial baseplate 114 rather than being rotatable/mobile. The spine 118 remains mobile, however, in that the spine 118 is rotatable with respect to the tibial baseplate 114 and the tibial insert 116. To facilitate spine rotation, the spine 118 passes through an aperture 160 of the tibial insert 116 with clearance on all sides.

The tibial baseplate 114 can include substantially vertical walls 199 extending proximally from a floor 198 of the tibial baseplate 114, which can act to secure the tibial insert 116 and keep the tibial insert 116 from moving during articulation of the knee. Although illustrated in this manner, the tibial insert 116 can be stabilized to a tibial baseplate 114 that does not have vertical walls 199. The tibial insert 116 can be fixed to the tibial baseplate 114 by gluing, cementing, fastening, clamping, interference fit, or any other practical means. Maintaining mobility (i.e., rotational freedom) of the spines 18, 118 can allow posterior cam surfaces 54, 154 (FIGS. 1B and 2B, respectively) to automatically maximize the contact area between the cam surfaces 54, 154 and the posterior femoral cam 36 (FIG. 1A) of the femoral component 12, in either a fixed- or mobile-bearing design. More particularly, as the posterior femoral cam 36 contacts the cam surface 154 of the spine 118 in deep flexion, the spines 18, 118 can rotate freely to seek the lowest-pressure configuration, which is the rotational spine orientation having the largest possible contact area.

Referring again to FIGS. 1A and 1B, using the spine 18 for illustration, this largest contact area can be achieved by the posterior femoral cam 36 contacting the relatively flat or large-radius posterior cam surface 54, as opposed to the smaller radius "corners" 55 bounding the medial and lateral edges of the cam surface 54. If the posterior femoral cam 36 does contact one of the corners 55, the spine 18 can be urged to rotate into a lower pressure configuration. Given that the spine 18 can rotate freely under this urging force, the spine 18 can continue to rotate until the lowest-pressure configuration is achieved, which can be the configuration in which the posterior femoral cam 36 creates a large-area contact with the posterior cam surface 54. In seeking this lowest-pressure configuration, the spine 18 can be said to "automatically" rotate under the pressure from the posterior femoral cam 36, and can therefore automatically adjust to accommodate internal and external rotation of the femur relative to the tibia.

Referring now to FIGS. 2A and 2B, an anterior cam 34 (see FIG. 6) formed in the femoral component 12 can impact the anterior surface 152 of the spine 118 in full extension or hyperextension prosthesis orientations, similarly causing the spine 118 to rotate and seek the largest-contact-area, lowest-pressure configuration. Advantageously, maintaining such large-area contact between the spine 118 and the femoral component 12 can lower contact pressures therebetween, thereby minimizing wear and maximizing longevity of the spine 118.

The spine 118 can include a distal portion 118A, an intermediate portion 118B and a proximal portion 118C. The distal portion 118A can be fully tapered, such that it engages the tibial stem 138 which can be correspondingly tapered along its entire length. The tapers of the distal spine portion 118A and the tibial stem 138 can be conical, and define a low-friction interface (such as a polymer-metal interface) to allow the spine 118 to rotate freely within the tibial stem 138. The taper of the distal spine portion 118A can be configured to have a taper angle that is slightly less than the taper angle of the tibial stem 138 to ensure a clearance fit and improve the mobility of the spine 118. The proximal portion 118C of the spine 118 can include the anterior surface 152 and the posterior cam surface 154, which can be similar to the surfaces 52, 54 (FIG. 1A), respectively.

An intermediate portion 118B of the spine 118 can have a generally non-tapered, cylindrical shape configured to pass through the aperture 160 formed in the tibial insert 116 with a slight clearance to facilitate free rotation of the spine 118. The cylindrical, non-tapered profile of the intermediate portion 118B can be highly resistant to anterior/posterior forces placed upon the spine 118 by a femoral component (such as femoral component 12 FIG. 1A) during articulation of the knee. For example, as the spine 118 is urged toward the adjacent interior wall of the aperture 160 of the tibial insert 116 by a force FC1 (FIG. 2B), such as by a posterior femoral cam 36 (FIG. 6) during articulation of the prosthesis 110 in vivo, the intermediate spine portion 118B can be urged into contact with the tibial insert 116. When such contact occurs, the "vertical" cylindrical wall can arrest any further deflection of the spine 118 by exerting a reaction force FC2, of the same magnitude as the force FC1, upon the intermediate portion 118B of the spine 118. Because the force FC2 is entirely horizontal, no significant force urges the spine 118 upwardly (i.e., proximally) or downwardly (i.e., distally). Thus, the spine 118 can be highly mechanically stable owing to its ability to remain fully seated within the tibial stem 138 and the aperture 160, even under heavy loads. This highly stable design can be appropriate for use in prostheses where high mechanical stability is beneficial, such as mid-level constraint designs, posterior stabilized designs, or any prostheses in which the forces on the proximal portion 118C of the spine 118 are relatively large.

Turning now to FIGS. 3A and 3B, another alternative example is shown. A fixed-bearing knee prosthesis 210 can be similar to the prosthesis 110 described above, with reference numerals of the prosthesis 210 having the same numerals used as the prosthesis 110 except with 100 added thereto. Structures of the prosthesis 210 correspond to similar structures denoted by corresponding reference numerals of the prostheses 10, 110 except as otherwise noted. The prosthesis 210 can include a tibial baseplate 214, a tibial insert 216, and a spine 218 arranged similarly to the prosthesis 110, but the prosthesis 210 is designed to accept a differently formed spine 218, as described below.

A distal portion 218A of the spine 218 can be similar to the distal portion 118A of the spine 118, in that both are tapered to be accommodated into the tapered cavity formed in the tibial stem 138, 238, respectively. Similarly, a proximal portion 218C of the spine 218 can include surfaces 252, 254 analogous to surfaces 152, 154 of the spine 118 (FIGS. 2A and 2B).

However, an intermediate portion 218B of the spine 218 can be slightly tapered as shown in FIGS. 3A and 3B, such that the outer face of the intermediate portion 218B is conical. An aperture 260 is correspondingly conical, with a similar clearance formed between the aperture 260 and the intermediate portion 218B. Although tapered, the intermediate portion 218B can define a smaller taper angle as compared to the distal portion 218A.

When a force FC1 is exerted upon the proximal portion 218C of the spine 218 (i.e., during flexion of the knee), the spine 218 can slightly deflect and come into contact with the tibial insert 216. However, owing to the conical shapes of the intermediate spine portion 218B and the aperture 260, the force exerted by the inner wall of the aperture 260 on the intermediate spine portion 218B can now be separated into a horizontal reaction force FC3H and a vertical reaction force FC3V (FIG. 3B), which is directed upwardly. Concurrently, the horizontal force FC3H transmitted between the spine 218 and the tibial insert 216 can be reduced as compared to the horizontal force FC1 arising from the non-tapered intermediate spine portion 118B (FIG. 2B), because some of the reaction force is dispersed in the upward direction. This reduction in horizontal force reduces friction between the spine 218 and the tibial insert 216. The spine 218 therefore has an enhanced rotational freedom as compared to the spine 118 (FIG. 2B), while maintaining a sufficient level of mechanical stability for many applications. For example, this stable, yet rotatably free design can be appropriate for use in prostheses in which a balance between mechanical stability and rotational freedom is desired, such as prostheses in which moderate forces are exerted on the proximal portion 218C of the spine 218 during articulation.

Figure 4A:
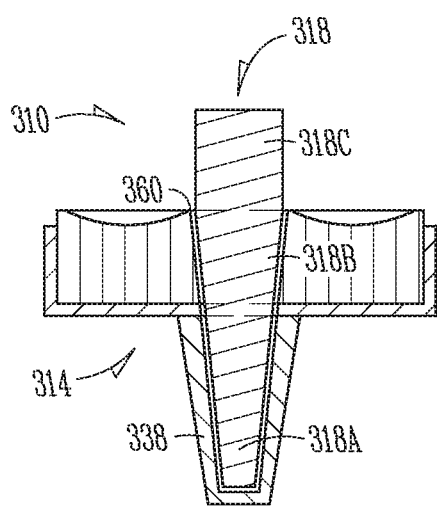
FIG. 4A is a front, cross-sectional view of a fixed-bearing knee prosthesis in accordance with the present disclosure, illustrating a fully-tapered intermediate spine portion.
Figure 4B:
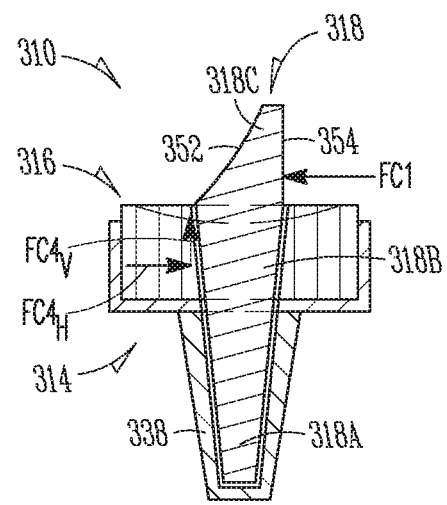
FIG. 4B is a side, cross-sectional view of the fixed-bearing knee prosthesis of FIG. 4A.

Turning to FIGS. 4A and 4B, a fixed-bearing prosthesis 310 can include a tibial baseplate 314, a cavity 338, a tibial insert 316, and a spine 318. The prosthesis 310 can be similar to the prosthesis 210, with reference numerals of the prosthesis 310 having the same numerals used as the prosthesis 210 except with 100 added thereto. Structures of the prosthesis 310 correspond to similar structures denoted by corresponding reference numerals of prostheses 10, 110, 210 (see FIGS. 1A-3B) except as otherwise noted.

A distal spine portion 318A can be tapered in a similar manner to the distal spine portions 118A, 218A described above. However, the prosthesis 310 can include a "fully tapered" spine 318, in that both the taper of the distal spine portion 318A carries over into an intermediate spine portion 318B, so that both portions 318A and 318B define one long tapered spine leading up to a proximal spine portion 318C. The proximal portion 318C of the spine 318 can include surfaces 352, 354 analogous to surfaces 152, 154 of the spine 118 (see FIG. 2B).

The taper angle in the intermediate spine portion 318B can direct some of the forces arising from contact between the intermediate portion 318B and an aperture 360 upwardly, similarly to the less-tapered intermediate spine portion 218B described above. However, the increased taper angle of the intermediate spine portion 318B can direct more force upwardly, thereby further reducing friction between the walls of the aperture 360 and the intermediate spine portion 318B. As schematically shown in FIG. 4B, the same force FC1 described above can be applied to the proximal spine portion 318C. The reaction forces can be made up of horizontal force FC4H and vertical force FC4V, similar to FC3H and FC3V described above with respect to the partially-tapered spine 218. However, owing to the greater taper in the intermediate spine portion 318B, FC4H can become a smaller constituent of the total reaction force, while FC4V can become a larger constituent. Thus, the spine 318 can have a high degree of rotational freedom and can most readily rotate during flexion of the knee prosthesis 310, because the lower horizontal force FC4H results in a lower friction between the wall of the aperture 360 and the intermediate spine portion 318B. This highly rotationally free design can be appropriate for use in prostheses where high mechanical stability is not required, such as prostheses in which relatively small forces are exerted on the proximal portion 318C of the spine 318 during articulation.

Figure 5A:
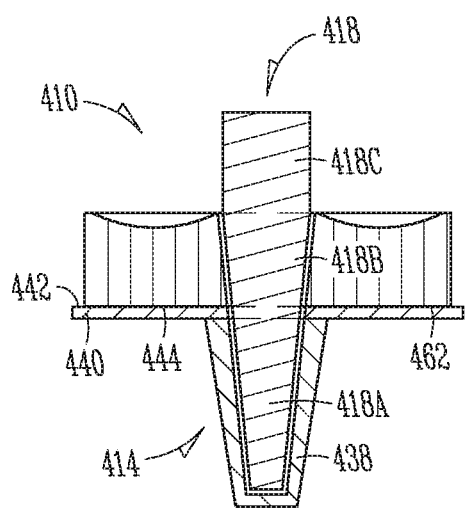
FIG. 5A is a front, cross-sectional view of a mobile-bearing knee prosthesis in accordance with the present disclosure.
Figure 5B:
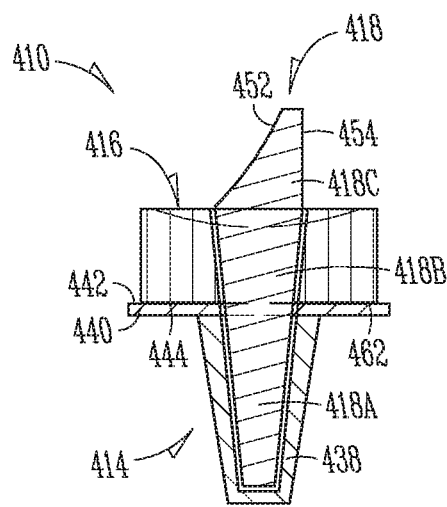
FIG. 5B is a side, elevation view of the mobile-bearing knee prosthesis of FIG. 5A.

Turning now to FIGS. 5A and 5B, a mobile-bearing prosthesis 410 can include a tibial baseplate 414, tibial insert 416, and spine 418. The prosthesis 410 can be similar to the prosthesis 310 in most respects, with reference numerals of the prosthesis 410 having the same numerals used as the prosthesis 310 except with 100 added thereto. Structures of the prosthesis 410 correspond to similar structures denoted by corresponding reference numerals of prostheses 10, 110, 210, 310 except as otherwise noted.

Similar to the tibial insert 16 (see FIG. 1A) described above, the tibial insert 416 of the prosthesis 410 can be rotatable with respect to the tibial baseplate 414 rather than fixed. The tibial insert 416 can define a distal surface 462 configured for articulation with a bearing surface 442 formed on the proximal side of a tibial plateau 440. The resulting interface 444 can have a low friction coefficient to promote smooth rotation of the tibial insert 416. An intermediate portion 418B of the spine 418 can rotatably articulate with an aperture 460 formed in the insert 416 in a similar manner as described above.

A distal portion 418A of the spine 418 can be similar to the distal portion 118A of the spine 118 (see FIG. 2B), in that both are tapered to be accommodated into the tapered cavity formed in tibial stems 138, 438, respectively. Similarly, a proximal portion 418C of the spine 418 can include anterior and posterior surfaces 452, 454 analogous to surfaces 152, 154 of the spine 118 (see FIG. 2B). Although the spine 418 is shown with a fully-tapered intermediate portion 418B, similar to the intermediate portion 318B of the spine 318, it is contemplated that the non-tapered spine portion 118B or the slightly-tapered spine portion 218B (see FIG. 3B) can also be used with a mobile-bearing prosthesis.

While the above discussion of rotatable spines 118, 218, 318, 418 has been in the context of fixed-bearing or rotatable-bearing prosthesis designs, it is contemplated that these same mobile-spine principles can be applied to mobile bearing designs in which the tibial insert is both rotatable and translatable with respect to the tibial baseplate. Translation of the tibial insert can be accomplished by having an aperture that allows anterior/posterior movement, lateral/medial movement or some combination of both directions of movement.

Figure 7:
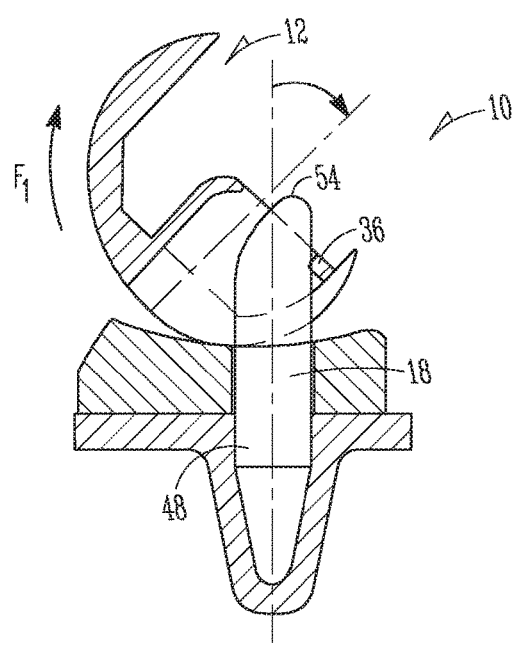
FIG. 7 is an elevation, section view of the knee joint prosthesis shown in FIG. 6, shown in a partial flexion orientation during a flexion motion.
Figure 8:
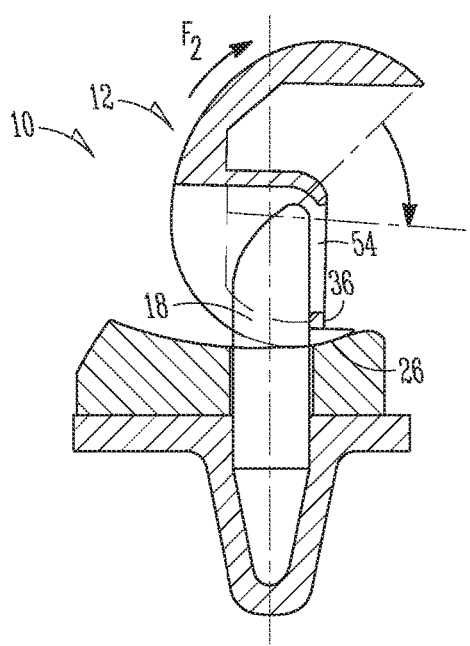
FIG. 8 is an elevation, partial section view of the knee joint prosthesis shown in FIG. 6, shown in a high flexion orientation during a flexion motion.

Referring now to FIGS. 6, 7, and 8, a knee prosthesis 10 can include a tibial baseplate 14, a tibial insert 16, and a spine 18. The knee prosthesis 10 can be similar to the prosthesis 10 described above with reference to FIGS. 1A and 1B. Structures of the prosthesis 10, as described with reference to FIGS. 6, 7, and 8 correspond to similar structures denoted by corresponding reference numerals of the prosthesis 10, as described with reference to FIGS. 1A and 1B, except as otherwise noted.

Referring to FIG. 6, the knee prosthesis 10 is shown in a full extension position of the knee joint. The spine 18 is located in the cavity 48 of the tibial baseplate 14. The spine 18 passes through the tibial insert 16 and occupies the intercondylar fossa 32 anterior to the posterior femoral cam 36. The posterior femoral cam 36 can be configured to be in contact with the posterior cam surface 54 at all times during joint movement or during portions of joint movement. As noted above, when the posterior femoral cam 36 applies force to the spine 18, the spine can rotate. In an example, an anterior cam 34 can extend from the femoral component 12. The anterior cam 34 can engage the anterior surface 52. The anterior cam 34 can prevent hyperextension of the knee joint and also can cause the spine 18 to rotate.

FIG. 7 illustrates a knee prosthesis 10 as the knee has started to flex and is shown at approximately a 45° flexion. F1 indicates a direction of movement of the femoral component 12. The posterior femoral cam 36 can engage the spine 18 at the posterior cam surface 54. The posterior cam surface 54 can be shaped to control relative movement between the posterior femoral cam 36 and the spine 18 and also the shape of the posterior cam surface 54 can influence the rotation of the spine 18 in the cavity 48.

FIG. 8 illustrates a knee prosthesis 10 as the knee has continued to flex and is shown at approximately a 90° flexion. F2 indicates a direction of movement of the femoral component 12. The posterior femoral cam 36 can engage the spine 18 at the posterior cam surface 54. The posterior femoral cam 36 can slide along the posterior cam surface 54 and is shown at a more distal position than the posterior femoral cam 36 of FIG. 7.

The above Detailed Description includes references to the accompanying drawings, which form a part of the Detailed Description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A knee joint prosthesis comprising:
a tibial baseplate comprising:
a tibial plateau comprising a proximal surface and an opposing distal surface; and
a tibial stem extending from the distal surface of the tibial plateau and including a cavity therein;
a fixed tibial insert disposable on the proximal surface of the tibial plateau, the fixed tibial insert including an aperture; and
a spine disposable in the cavity and extendable through the aperture from the proximal surface of the tibial plateau, the spine rotatable with respect to the tibial baseplate and the fixed tibial insert, the spine and the fixed tibial insert shaped to guide rollback of the knee joint prosthesis.

2. The knee joint prosthesis of claim 1, wherein the spine and the fixed tibial insert are shaped to guide asymmetric anteroposterior rollback.

3. The knee joint prosthesis of claim 2, wherein the asymmetric anteroposterior rollback comprises rollback of a lateral femoral condyle at a faster rate than rollback of a medial femoral condyle.

4. The knee joint prosthesis of claim 1, wherein the spine and the fixed tibial insert are shaped to guide rollback of the knee joint prosthesis along a specific motion profile during flexion.

5. The knee joint prosthesis of claim 1, wherein the spine is configured to automatically rotate under pressure to accommodate internal and external rotation of a femur relative to a tibia.

6. The knee joint prosthesis of claim 1, wherein the spine includes an intermediate spine portion, disposed within the aperture of the fixed tibial insert, configured to rotatably articulate with a wall of the aperture.

7. The knee joint prosthesis of claim 6, wherein the spine includes a distal spine portion, disposed within the cavity of the tibial stem, having a tapered, substantially conical shape.

8. The knee joint prosthesis of claim 7, wherein at least one of the intermediate spine portion and the distal spine portion includes a sleeve coupled about an outer spine surface.

9. The knee joint prosthesis of claim 1, wherein the fixed tibial insert includes a sleeve coupled to a surface of the aperture.

10. The knee joint prosthesis of claim 1, wherein the tibial stem includes a sleeve coupled to a surface of the cavity.

11. A knee joint prosthesis comprising:
a tibial baseplate comprising:
a tibial plateau comprising a proximal surface and an opposing distal surface; and
a tibial stem extending from the distal surface of the tibial plateau and including a cavity therein;
a tibial insert located on the proximal surface of the tibial plateau and removably engageable therewith, the tibial insert including an aperture;
a femoral component including a lateral condyle, a medial condyle, and an intercondylar fossa disposed between the lateral and medial condyles, the femoral component articulable on the tibial insert; and
a spine disposable in the cavity and extendable through the aperture from the proximal surface of the tibial plateau, the spine comprising a posterior cam surface engageable with the femoral component, the spine rotatable with respect to the tibial baseplate and the tibial insert to guide rollback of the knee joint prosthesis.

12. The knee joint prosthesis of claim 11, wherein the spine and the tibial insert are shaped to guide asymmetric anteroposterior rollback.

13. The knee joint prosthesis of claim 12, wherein the asymmetric anteroposterior rollback comprises rollback of the lateral condyle at a faster rate than rollback of the medial condyle.

14. The knee joint prosthesis of claim 11, wherein the spine and the tibial insert are shaped to guide rollback of the knee joint along a specific motion profile during flexion.

15. The knee joint prosthesis of claim 11, the femoral component further comprising a posterior femoral cam engageable with the posterior cam surface.

16. The knee joint prosthesis of claim 15, wherein the posterior cam surface and the posterior femoral cam are configured to guide rollback during engagement.

17. The knee joint prosthesis of claim 15, wherein the spine is configured to automatically rotate under pressure from the posterior femoral cam to accommodate internal and external rotation of the femur relative to the tibia.

18. The knee joint prosthesis of claim 11, wherein the tibial insert is a fixed bearing.

19. The knee joint prosthesis of claim 11, wherein the tibial insert is a mobile bearing.

* * * * *